(12) United States Patent
Kokish et al.

(10) Patent No.: US 7,794,777 B2
(45) Date of Patent: Sep. 14, 2010

(54) METHOD FOR REDUCING STENT COATING DEFECTS

(75) Inventors: Arkady Kokish, Los Gatos, CA (US); Charles Snyder, San Francisco, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 267 days.

(21) Appl. No.: 12/024,932

(22) Filed: Feb. 1, 2008

(65) Prior Publication Data

US 2008/0124452 A1 May 29, 2008

Related U.S. Application Data

(62) Division of application No. 10/376,027, filed on Feb. 26, 2003, now Pat. No. 7,354,480.

(51) Int. Cl.
 *B05D 3/12* (2006.01)
 *B05D 1/02* (2006.01)
 *B05C 13/00* (2006.01)

(52) U.S. Cl. .................... 427/2.1; 427/2.24; 427/421.1; 427/424; 427/427.4; 118/500

(58) Field of Classification Search ................ 427/2.1, 427/2.24, 421.1, 424, 427.1, 427.4; 118/500
See application file for complete search history.

(56) References Cited

U.S. PATENT DOCUMENTS

| | | | |
|---|---|---|---|
| 4,629,563 A | 12/1986 | Wrasidlo | |
| 4,733,665 A | 3/1988 | Palmaz | |
| 4,800,882 A | 1/1989 | Gianturco | |
| 4,886,062 A | 12/1989 | Wiktor | |
| 4,906,423 A | 3/1990 | Frisch | |
| 5,037,427 A | 8/1991 | Harada et al. | |
| 5,171,445 A | 12/1992 | Zepf | |
| 5,188,734 A | 2/1993 | Zepf | |
| 5,229,045 A | 7/1993 | Soldani | |
| 5,234,457 A | 8/1993 | Andersen | |
| 5,537,729 A | 7/1996 | Kolobow | |
| 5,611,775 A | 3/1997 | Machold et al. | |
| 5,624,411 A | 4/1997 | Tuch | |
| 5,628,786 A | 5/1997 | Banas et al. | |
| 5,772,864 A | 6/1998 | Møller et al. | |
| 5,788,626 A | 8/1998 | Thompson | |
| 5,820,917 A | 10/1998 | Tuch | |
| 5,823,996 A | 10/1998 | Sparks | |
| 5,833,659 A | 11/1998 | Kranys | |
| 5,855,598 A | 1/1999 | Pinchuk | |

(Continued)

FOREIGN PATENT DOCUMENTS

JP 05009726 1/1993

OTHER PUBLICATIONS

U.S. Appl. No. 10/255,913, filed Sep. 26, 2002, Tang et al.
U.S. Appl. No. 10/304,669, filed Nov. 25, 2002, Madriaga et al.

*Primary Examiner*—Timothy H Meeks
*Assistant Examiner*—Cachet I Sellman
(74) *Attorney, Agent, or Firm*—Squire, Sanders & Dempsey, L.L.P.

(57) ABSTRACT

A stent mandrel fixture and method for supporting a stent during the application of a coating substance is provided.

19 Claims, 2 Drawing Sheets

U.S. PATENT DOCUMENTS

| | | | |
|---|---|---|---|
| 5,865,814 A | 2/1999 | Tuch | |
| 5,895,407 A | 4/1999 | Jayaraman | |
| 5,897,911 A | 4/1999 | Loeffler | |
| 5,922,393 A | 7/1999 | Jayaraman | |
| 5,935,135 A | 8/1999 | Bramfitt et al. | |
| 5,948,018 A | 9/1999 | Dereume et al. | |
| 6,010,573 A | 1/2000 | Bowlin | |
| 6,045,899 A | 4/2000 | Wang et al. | |
| 6,056,993 A | 5/2000 | Leidner et al. | |
| 6,120,847 A | 9/2000 | Yang et al. | |
| 6,126,686 A | 10/2000 | Badylak et al. | |
| 6,153,252 A | 11/2000 | Hossainy et al. | |
| 6,156,373 A | 12/2000 | Zhong et al. | |
| 6,214,115 B1 | 4/2001 | Taylor et al. | |
| 6,245,099 B1 | 6/2001 | Edwin et al. | |
| 6,258,121 B1 | 7/2001 | Yang et al. | |
| 6,279,368 B1 | 8/2001 | Escano et al. | |
| 6,322,847 B1 | 11/2001 | Zhong et al. | |
| 6,364,903 B2 | 4/2002 | Tseng et al. | |
| 6,387,118 B1 | 5/2002 | Hanson | |
| 6,395,326 B1 | 5/2002 | Castro et al. | |
| 6,517,889 B1 * | 2/2003 | Jayaraman | 427/2.24 |
| 6,521,284 B1 | 2/2003 | Parsons et al. | |
| 6,527,863 B1 * | 3/2003 | Pacetti et al. | 118/500 |
| 6,544,582 B1 | 4/2003 | Yoe | |
| 6,565,659 B1 | 5/2003 | Pacetti et al. | |
| 6,572,644 B1 | 6/2003 | Moein | |
| 6,605,154 B1 * | 8/2003 | Villareal | 118/500 |
| 6,673,154 B1 | 1/2004 | Pacetti et al. | |
| 6,695,920 B1 * | 2/2004 | Pacetti et al. | 118/500 |
| 6,818,063 B1 * | 11/2004 | Kerrigan | 118/500 |
| 7,416,609 B1 * | 8/2008 | Madriaga et al. | 118/500 |
| 2002/0019599 A1 * | 2/2002 | Rooney et al. | 600/585 |

* cited by examiner

METHOD FOR REDUCING STENT COATING DEFECTS

This application is a divisional application of U.S. application Ser. No. 10/376,027, filed Feb. 26, 2003 now U.S. Pat. No. 7,354,480, which is incorporated herein by reference in its entirety.

TECHNICAL FIELD

This invention relates generally to a method of coating a stent, and more particularly, but not exclusively, to a method of coating a stent using a stent support assembly movable relative to the stent while a coating is applied to the stent.

BACKGROUND

Blood vessel occlusions are commonly treated by mechanically enhancing blood flow in the affected vessels, such as by employing a stent. Stents act as scaffoldings, functioning to physically hold open and, if desired, to expand the wall of affected vessels. Typically stents are capable of being compressed, so that they can be inserted through small lumens via catheters, and then expanded to a larger diameter once they are at the desired location. Examples in the patent literature disclosing stents include U.S. Pat. No. 4,733,665 issued to Palmaz, U.S. Pat. No. 4,800,882 issued to Gianturco, and U.S. Pat. No. 4,886,062 issued to Wiktor.

FIG. 1 illustrates a conventional stent 10 formed from a plurality of struts 12. The plurality of struts 12 are radially expandable and interconnected by connecting elements 14 that are disposed between adjacent struts 12, leaving lateral openings or gaps 16 between adjacent struts 12. The struts 12 and the connecting elements 14 define a tubular stent body having an outer, tissue-contacting surface and an inner surface.

Stents are used not only for mechanical intervention but also as vehicles for providing biological therapy. Biological therapy can be achieved by medicating the stents. Medicated stents provide for the local administration of a therapeutic substance at the diseased site. Local delivery of a therapeutic substance is a preferred method of treatment because the substance is concentrated at a specific site and thus smaller total levels of medication can be administered in comparison to systemic dosages that often produce adverse or even toxic side effects for the patient.

One method of medicating a stent involves the use of a polymeric carrier coated onto the surface of the stent. A composition including a solvent, a polymer dissolved in the solvent, and a therapeutic substance dispersed in the blend is applied to the stent by immersing the stent in the composition or by spraying the composition onto the stent. The solvent is allowed to evaporate, leaving on the stent strut surfaces a coating of the polymer and the therapeutic substance impregnated in the polymer.

A shortcoming of the above-described method of medicating a stent is the potential for coating defects. While some coating defects can be minimized by adjusting the coating parameters, other defects occur due to the nature of the interface between the stent and the apparatus on which the stent is supported during the coating process. A high degree of surface contact between the stent and the supporting apparatus can provide regions in which the liquid composition can flow, wick, and collect as the composition is applied. As the solvent evaporates, the excess composition hardens to form excess coating at and around the contact points between the stent and the supporting apparatus. Upon the removal of the coated stent from the supporting apparatus, the excess coating may stick to the apparatus, thereby removing some of the coating from the stent and leaving bare areas. Alternatively, the excess coating may stick to the stent, thereby leaving excess coating as clumps or pools on the struts or webbing between the struts.

Accordingly, a new stent mandrel fixture and method are needed to minimize coating defects.

SUMMARY

Briefly and in general terms, the present invention is directed to a method of coating a stent. In aspects of the present invention, the method comprises inserting a mandrel having a coil member through a longitudinal bore of a stent, wherein the stent is supported on the coil member, and applying a coating composition to the stent to form a coating. In detailed aspects, the coil member prevents an outer surface of the mandrel from making contact with an inner surface of the stent during the application of the coating composition.

In other aspects of the present invention, the method comprises positioning a stent on a support assembly, the support assembly comprising a first member extending through a longitudinal bore of a stent, a second member coupled to one end of the first member, and a third member coupled to the other end of the first member. The method further comprises applying an atomized coating composition from a nozzle assembly to the stent, and rotating the support assembly to rotate the stent about the longitudinal axis of the stent, wherein during the act of rotating, the atomized coating composition reflects off of the second member to move the stent towards the third member and the atomized coating composition reflects off of the third member to move the stent towards the second member. In detailed aspects, the second member and third member include sloping sides facing the stent for receiving and reflecting the atomized coating composition onto the stent. When the sloping side of the second member is facing the nozzle assembly, the sloping side of the third member is facing away from the nozzle assembly. When the sloping side of the third member is facing the nozzle assembly, the sloping side of the second member is facing away from the nozzle assembly.

In yet other aspects of the present invention, the method comprises supporting a stent on a support assembly so that there is an area of contact on the stent that contacts the support assembly, applying a coating composition on the stent, and changing the area of contact while applying the coating composition to reduce or prevent the coating composition from gathering between the stent and the support assembly. In detailed aspects, changing the area of contact includes moving either one of the stent and the support assembly relative to the other one of the stent and the support assembly.

The features and advantages of the invention will be more readily understood from the following detailed description which should be read in conjunction with the accompanying drawings.

BRIEF DESCRIPTION OF THE DRAWINGS

Non-limiting and non-exhaustive embodiments of the present invention are described with reference to the following figures, wherein like reference numerals refer to like parts throughout the various views unless otherwise specified.

DETAILED DESCRIPTION

The following description is provided to enable any person having ordinary skill in the art to make and use the invention, and is provided in the context of a particular application and its requirements. Various modifications to the embodiments will be readily apparent to those skilled in the art, and the generic principles defined herein may be applied to other embodiments and applications without departing from the spirit and scope of the invention. Thus, the present invention is not intended to be limited to the embodiments shown, but is to be accorded the widest scope consistent with the principles, features and teachings disclosed herein.

Figure 1:
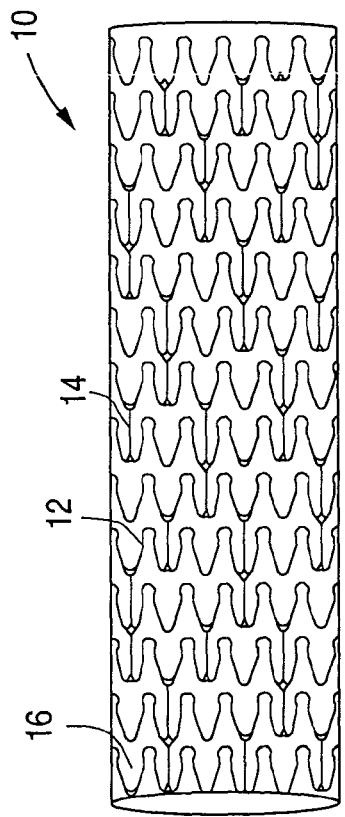
FIG. 1 illustrates a conventional stent.
Figure 2:
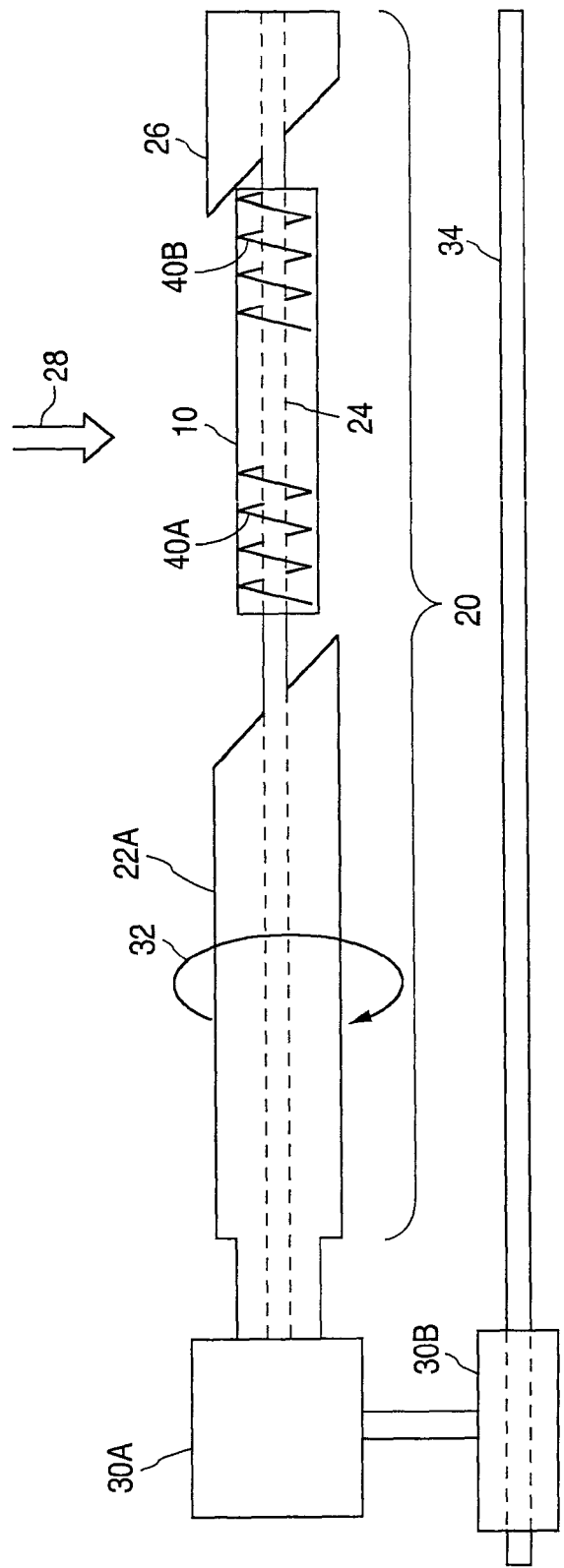
FIG. 2 illustrates a stent mandrel fixture in accordance with an embodiment of the invention.

FIG. 2 illustrates a stent mandrel fixture 20 in accordance with an embodiment of the invention. The fixture 20 for supporting the stent 10 is illustrated to include a support member 22A, a mandrel 24, a wire, coil or springs 40A and 40B, and a lock member 26. The support member 22A can connect to a motor 30A so as to provide rotational motion about the longitudinal axis of the stent 10, as depicted by arrow 32, during a coating process. Another motor 30B can also be provided for moving the mandrel fixture 20 in a linear direction, back and forth, along a rail 34.

The wires 40A and 40B extend from the mandrel 24 and circumscribe the mandrel 24 and support the stent 10 during a coating process. The wires 40A and 40B can be short springs of 2-5 coils each and made from about 0.006 to about 0.008 inch diameter wire. The diameter of the wire varies based on the stent 10 characteristics. In one embodiment, the outer diameter of the springs 40A and 40B can be less than the inner diameter of the stent 10 (as mounted on the coils 40A and 40B) for allowing the stent 10 to move telescopically back and forth between support member 22A and lock member 26, as will be described below. With smaller diameter coils 40A and 40B, the angular speed of the stent 10 as compared to the coils 40A and 40B is obviously different. The combination of linear as well as rotational movement of the stent 10 relative to the coils 40A and 40B reduces or eliminates the gathering of coating composition between the two components. The springs 40A and 40B can be made from or coated with a non-stick material such as TEFLON. It will be appreciated by one of ordinary skill in the art that additional or fewer springs can be used. It should be also noted, however, that the use of springs 40A and 40B is not required. In one alternative embodiment, the mandrel 24 can have a duel diameter, such that the stent 10 rests on the segment of the mandrel 24 having the bigger diameter. In yet another embodiment of the invention, the stent 10 can be securely pinched between support member 22A and lock member 26 during the coating process.

Figure 3:
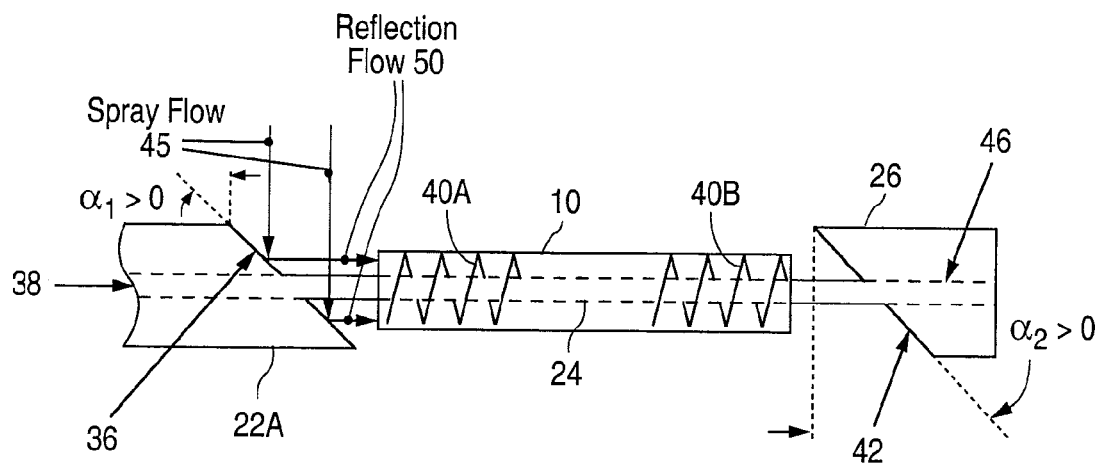
FIG. 3 illustrates another view of stent mandrel fixture of FIG. 2.

Referring to FIG. 3, support member 22A includes a sloping side or end portion 36, tapering at an angle $\alpha_1$ of about 15° to about 75°, more narrowly from about 30° to about 60°. By way of example, the angle $\alpha_1$ can be about 45°. In accordance with one embodiment of the invention, the mandrel 24 can be permanently affixed to the sloping end portion 36. Alternatively, the support member 22A can include a bore 38 for receiving a first end of the mandrel 24. The first end of mandrel 24 can be threaded to screw into the bore 38 or, alternatively, can be retained within the bore 38 by a friction fit. The bore 38 should be deep enough so as to allow the mandrel 24 to securely mate with the support member 22A. The depth of the bore 38 can also be over-extended so as to allow a significant length of the mandrel 24 to penetrate or screw into the bore 38. This would allow the length of mandrel 24 to be adjusted to accommodate stents of various sizes.

The outer diameter of the mandrel 24 is smaller than the inner diameter of the stent 10 so as to prevent the outer surface of the mandrel 24 from making contact with the inner surface of the stent 10. A sufficient clearance between the outer surface of the mandrel 24 and the inner surface of the stent 10 should be provided to prevent the mandrel 24 from obstructing the pattern of the stent 10 body during the coating process. If the stent 10 is not securely pinched between the support member 22A and the lock member 26, the required clearance can be provided by the springs 40A and 40B, which can support the stent 10 without obstructing the pattern of the stent 10 body during the coating process. By way of example, the outer diameter of mandrel 24 can be from about 0.010 inches (0.254 mm) to about 0.021 inches (0.533 mm) when the stent 10 has an inner diameter of between about 0.025 inches (0.635 mm) and about 0.035 inches (0.889 mm). In addition, the length of the mandrel 24 is longer than that of stent 10 to be coated.

The lock member 26 includes a sloping side or end portion 42 having a tapered angle $\alpha_2$. The angle $\alpha_2$ can be the same as or different from the angle $\alpha_1$. A second end of the mandrel 24 can be permanently affixed to the lock member 26 if the first end is disengagable from the support member 22A. Alternatively, in accordance with another embodiment, the mandrel 24 can have a threaded second end for screwing into a bore 46 of the lock member 26. The bore 46 can be of any suitable depth that would allow the lock member 26 to be incrementally moved closer to the support member 22A. In accordance with yet another embodiment, a non-threaded second end of the mandrel 24 and the bore 46 combination can be employed such that the second end can be press-fitted or friction-fitted within the bore 46.

During a coating process, a spray flow 45, discharged from a nozzle assembly 28, comprising a coating composition (and atomizing air, if the composition is atomized), deflects off of the surface of the sloping end 36 of the support member 22A to become a reflection flow 50. The sloping end 36 receives and deflects the composition when the surface of the sloping end 36 is facing the nozzle assembly 28 or the direction from which the spray flow 45 is discharged. When sloping end 36 is facing the nozzle assembly 28, the sloping end 42 of the locking member 26 is facing away from the nozzle assembly 28 so as not to interfere with the movement of the stent 10 by deflecting the coating composition at the stent. This reflection flow 50 pushes the stent 10 in an axial direction away from the support member 22A. When engine 30A rotates the fixture 20 and the stent 10 (optionally in combination with the engine 30B moving the locking member 26) so as to place the locking member 26 in position to intersect the spray flow 45 on the surface of the sloping end 42, the spray flow 45 bounces off of the surface of the sloping end 42 to push the stent 10 back towards the support member 22A. Accordingly, the stent 10 can be displaced back and forth between the support member 22A and the locking member 26 during the rotation of the fixture 20. As a result, the contact between the support device and the stent 10 is not a fixed region such that damage to a coating film deposited on the stent is reduced or eliminated.

The components of the coating substance or composition can include a solvent or a solvent system comprising multiple solvents, a polymer or a combination of polymers, a therapeutic substance or a drug or a combination of drugs. The composition can be used to coat stents or other implantable medical devices. Representative examples of polymers that can be used to coat a stent or medical device include ethylene vinyl alcohol copolymer (commonly known by the generic name EVOH or by the trade name EVAL); poly(hydroxyvalerate); poly(L-lactic acid); polycaprolactone; poly(lactide-co-glycolide); poly(glycerol-sebacate); poly(hydroxybutyrate); poly(hydroxybutyrate-co-valerate); polydioxanone; polyorthoester; polyanhydride; poly(glycolic acid); poly(D,L-lactic acid); poly(glycolic acid-co-trimethylene carbonate); polyphosphoester; polyphosphoester urethane; poly(amino acids); cyanoacrylates; poly(trimethylene carbonate); poly(iminocarbonate); copoly(ether esters) (e.g. PEO/PLA); polyalkylene oxalates; polyphosphazenes; biomolecules, such as fibrin, fibrinogen, cellulose, starch, collagen and hyaluronic acid; polyurethanes; silicones; polyesters; polyolefins; polyisobutylene and ethylene-alphaolefin copolymers; acrylic polymers and copolymers; vinyl halide polymers and copolymers, such as polyvinyl chloride; polyvinyl ethers, such as polyvinyl methyl ether; polyvinylidene halides, such as polyvinylidene fluoride and polyvinylidene chloride; polyacrylonitrile; polyvinyl ketones; polyvinyl aromatics, such as polystyrene; polyvinyl esters, such as polyvinyl acetate; copolymers of vinyl monomers with each other and olefins, such as ethylene-methyl methacrylate copolymers, acrylonitrilestyrene copolymers, ABS resins, and ethylene-vinyl acetate copolymers; polyamides, such as Nylon 66 and polycaprolactam; alkyd resins; polycarbonates; polyoxymethylenes; polyimides; polyethers; epoxy resins; polyurethanes; rayon; rayon-triacetate; cellulose; cellulose acetate; cellulose butyrate; cellulose acetate butyrate; cellophane; cellulose nitrate; cellulose propionate; cellulose ethers; and carboxymethyl cellulose.

"Solvent" is defined as a liquid substance or composition that is compatible with the polymer and is capable of dissolving the polymer at the concentration desired in the composition. Examples of solvents include, but are not limited to, dimethylsulfoxide, chloroform, acetone, water (buffered saline), xylene, methanol, ethanol, 1-propanol, tetrahydrofuran, 1-butanone, dimethylformamide, dimethylacetamide, cyclohexanone, ethyl acetate, methylethylketone, propylene glycol monomethylether, isopropanol, isopropanol admixed with water, N-methyl pyrrolidinone, toluene, and mixtures and combinations thereof.

The therapeutic substance or drug can be for inhibiting the activity of vascular smooth muscle cells. More specifically, the active agent can be aimed at inhibiting abnormal or inappropriate migration and/or proliferation of smooth muscle cells for the inhibition of restenosis. The active agent can also include any substance capable of exerting a therapeutic or prophylactic effect in the practice of the present invention. For example, the agent can be for enhancing wound healing in a vascular site or improving the structural and elastic properties of the vascular site. Examples of agents include antiproliferative substances such as actinomycin D, or derivatives and analogs thereof (manufactured by Sigma-Aldrich 1001 West Saint Paul Avenue, Milwaukee, Wis. 53233; or COSMEGEN available from Merck). Synonyms of actinomycin D include dactinomycin, actinomycin IV, actinomycin $I_1$, actinomycin $X_1$, and actinomycin $C_1$. The active agent can also fall under the genus of antineoplastic, antiinflammatory, antiplatelet, anticoagulant, antifibrin, antithrombin, antimitotic, antibiotic, antiallergic and antioxidant substances. Examples of such antineoplastics and/or antimitotics include paclitaxel (e.g. TAXOL® by Bristol-Myers Squibb Co., Stamford, Conn.), docetaxel (e.g. Taxotere®, from Aventis S.A., Frankfurt, Germany) methotrexate, azathioprine, vincristine, vinblastine, fluorouracil, doxorubicin hydrochloride (e.g. Adriamycin® from Pharmacia & Upjohn, Peapack N.J.), and mitomycin (e.g. Mutamycin® from Bristol-Myers Squibb Co., Stamford, Conn.). Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, and thrombin inhibitors such as Angiomax™ (Biogen, Inc., Cambridge, Mass.). Examples of such cytostatic or antiproliferative agents include angiopeptin, angiotensin converting enzyme inhibitors such as captopril (e.g. Capoten® and Capozide® from Bristol-Myers Squibb Co., Stamford, Conn.), cilazapril or lisinopril (e.g. Prinivil® and Prinzide® from Merck & Co., Inc., Whitehouse Station, N.J.); calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), and nitric oxide. An example of an antiallergic agent is permirolast potassium. Other therapeutic substances or agents which may be appropriate include alpha-interferon, genetically engineered epithelial cells, dexamethasone, and rapamycin.

Figure 4:
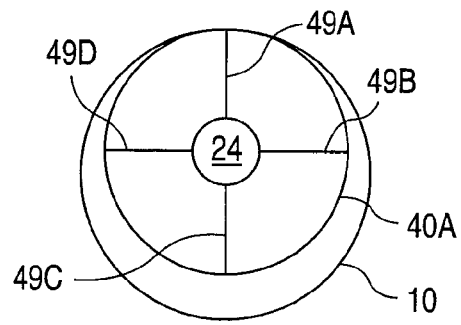
FIG. 4 illustrates a cross section a portion of the stent mandrel fixture of FIG. 2.

FIG. 4 illustrates a cross section a portion of the stent mandrel fixture 20 of FIG. 2. Shown in FIG. 4 is the mandrel 24 circumscribed (at least on revolution) by the coil 40A. The spring 40A has an outer diameter greater than an outer diameter of the mandrel 24 but less than the inner diameter of the stent 10. The spring 40A can include a plurality of support structures, e.g., 49A, 49B, 49C, and 49D that extend inwards from the spring 40A to contact the mandrel 24. The support structures 49A-49D support the spring 40A so that the coils of the spring 40A support the stent 10 without the stent 10 coming into contact with the surface of the mandrel 24. It will be appreciated by one of ordinary skill in the art that fewer (i.e., 3) or additional support structures can be used. It will be further appreciated that the spring 40B can be substantially similar to the spring 40A.

Figure 5:
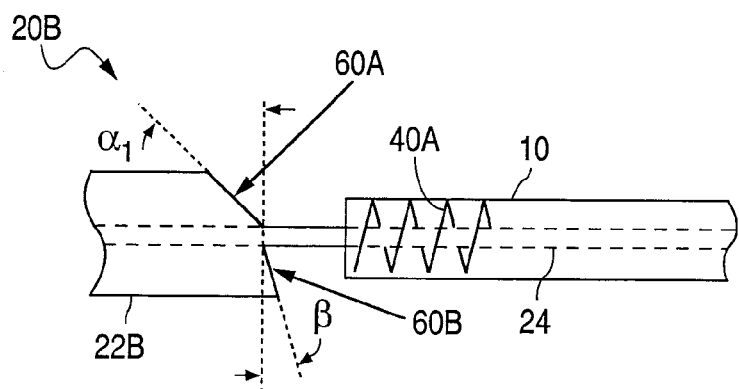
FIG. 5 illustrates a stent mandrel fixture in accordance with another embodiment of the invention.

FIG. 5 illustrates a stent mandrel fixture 20B in accordance with another embodiment of the invention. The stent mandrel fixture includes a support member 22B, mandrel 24 and a locking member (not shown) that can be substantially similar to the locking member 26. The support member 22B is substantially similar to the support member 22A except that the sloping side of the support member 22B comprises two separate walls or surfaces 60A and 60B. The sloping surface 60A can have an angle $\alpha_1$ (i.e., the same as the angle $\alpha_1$ of the sloping end 36) and the sloping surface 60B can have an angle of $\beta$, wherein $\beta$ is less than $\alpha_1$ (i.e., steeper). During a spray coating process, when the sloping surface 60A is facing the spray flow (due to rotation) of a nozzle, the surface 60A deflects the spray flow and atomized air against the stent 10, thereby pushing the stent 10 in an axial direction away from the surface 60A. When the support member 22B has rotated 180° the sloping surface 60B minimizes shadowing of the stent 10 from the spray flow, thereby ensuring an even coating on the stent 10. It will be appreciated by one of ordinary skill in the art that the locking member of the stent mandrel fixture 20B can have a sloping end substantially similar to the sloping end of the support member 22B.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A method of coating a stent, comprising:
   inserting a mandrel having a coil member through a longitudinal bore of a stent, wherein the stent is supported on the coil member; and
   applying a coating composition to the stent to form a coating, wherein the coil member prevents an outer surface of the mandrel from making contact with an inner surface of the stent during the application of the coating composition.

2. The method of claim 1, wherein the coating composition comprises a polymer dissolved in a solvent and optionally a therapeutic substance added thereto.

3. The method of claim 1, wherein the mandrel includes a first member connected to one end of the mandrel and a second member connected to an opposition end of the mandrel for preventing the stent from sliding off of the mandrel.

4. The method of claim 3, wherein mandrel extends from a side of the first member or a side of the second member at an angle other than 90 degrees.

5. The method of claim 1, wherein the stent contacts the coil member.

6. A method of coating a stent, comprising:
   positioning a stent on a support assembly, the support assembly comprising a first member extending through a longitudinal bore of a stent, a second member coupled to one end of the first member, and a third member coupled to the other end of the first member;
   applying an atomized coating composition from a nozzle assembly to the stent; and
   rotating the support assembly to rotate the stent about the longitudinal axis of the stent, wherein during the act of rotating, the atomized coating composition reflects off of the second member to move the stent towards the third member and the atomized coating composition reflects off of the third member to move the stent towards the second member.

7. The method of claim 6, wherein the second member and third member include sloping sides facing the stent for receiving and reflecting the atomized coating composition onto the stent, wherein when the sloping side of the second member is facing the nozzle assembly, the sloping side of the third member is facing away from the nozzle assembly and when the sloping side of the third member is facing the nozzle assembly, the sloping side of the second member is facing away from the nozzle assembly.

8. The method of claim 7, wherein when the sloping side of the second member is facing the nozzle assembly, the coating composition reflects off of a surface of the sloping side of the second member to move the stent towards the third member and when the sloping side of the third member is facing the nozzle assembly, the coating composition reflects off of a surface of the sloping side of the third member to move the stent towards the second member.

9. The method of claim 7, wherein the sloping sides are capable of reflecting the atomized coating composition for moving the stent only when the sloping sides are facing the nozzle assembly.

10. The method of claim 6, wherein the movement of the stent between the second and third members is repeated numerous times during each coating application process.

11. The method of claim 6, wherein when the coating composition reflects off of the second member to move the stent towards the third member, the coating composition is not capable of reflecting off of the third member for moving the stent towards the second member;
   and wherein when the coating composition reflects off of the third member to move the stent toward the second member, the coating composition is not capable of reflecting off of the second member for moving the stent towards the third member.

12. A method of coating a stent, comprising:
   supporting a stent on a support assembly so that there is an area of contact on the stent that contacts a coil member on the support assembly;
   applying a coating composition on the stent; and
   changing the area of contact while applying the coating composition to reduce or prevent the coating composition from gathering between the stent and the support assembly.

13. A method of coating a stent, comprising:
   supporting a stent on a support assembly so that there is an area of contact on the stent that contacts the support assembly;
   applying a coating composition on the stent; and
   changing the area of contact while applying the coating composition to reduce or prevent the coating composition from gathering between the stent and the support assembly, wherein applying the coating composition on the stent includes directing the coating composition along a flow direction toward the support assembly, and changing the area of contact includes deflecting at least some of the coating composition directed along the flow direction off of a first surface of the support assembly, the first surface oriented at an angle other than ninety degrees to the flow direction so that the deflected coating composition moves the stent away from the first surface.

14. A method of coating a stent, comprising:
   supporting a stent on a support assembly so that there is an area of contact on the stent that contacts the support assembly;
   applying a coating composition on the stent; and
   changing the area of contact while applying the coating composition to reduce or prevent the coating composition from gathering between the stent and the support assembly, wherein changing the area of contact includes deflecting at least some of the coating composition directed along the flow direction off of a second surface of the support assembly, the second surface oriented at an angle other than ninety degrees to the flow direction so that the coating composition deflected from the second surface moves the stent toward the first surface.

15. The method of claim 14, wherein when at least some of the coating composition is deflected off of the first surface, the second surface does not face the flow direction of the coating composition and the coating composition is not deflected off of the second surface.

16. The method of claim 14, wherein deflecting at least some of the coating composition off of the second surface includes rotating the second surface so that it faces the flow direction of the coating composition.

17. The method of claim 14, wherein supporting the stent on the support assembly includes placing the stent in contact with a coil member of the support assembly.

18. A method of coating a stent, comprising:

supporting a stent on a support assembly so that there is an area of contact on the stent that contacts the support assembly;

applying a coating composition on the stent; and changing the area of contact while applying the coating composition to reduce or prevent the coating composition from gathering between the stent and the support assembly, wherein the support assembly includes a coil member contacting the stent, the coil member having an outer diameter less than the inner diameter of the stent, and wherein changing the area of contact includes rotating coil member and the stent so that the coil member rotates at an angular speed different than the stent.

19. A method of coating a stent, comprising:

supporting a stent on a support assembly so that there is an area of contact on the stent that contacts the support assembly;

applying a coating composition on the stent; and changing the area of contact while applying the coating composition to reduce or prevent the coating composition from gathering between the stent and the support assembly, wherein the support assembly includes a coil member contacting the stent, and wherein changing the area of contact includes causing a combination of linear and rotational movement of the stent relative to the coil member.

* * * * *